(12) United States Patent
Muller et al.

(10) Patent No.: US 11,246,511 B2
(45) Date of Patent: Feb. 15, 2022

(54) SYSTEM FOR ANALYZING A PATIENT USING A TRANSCUTANEOUS SENSOR

(71) Applicant: EyeSense GmbH, Grossostheim (DE)

(72) Inventors: Achim Muller, Grossostheim (DE); Tom Meissner-Braun, Uberlingen (DE); Matthias Pischan, Darmstadt (DE)

(73) Assignee: EyeSense GmbH, Grossostheim (DE)

( * ) Notice: Subject to any disclaimer, the term of this patent is extended or adjusted under 35 U.S.C. 154(b) by 226 days.

(21) Appl. No.: 16/253,668

(22) Filed: Jan. 22, 2019

(65) Prior Publication Data

US 2019/0223769 A1 Jul. 25, 2019

(30) Foreign Application Priority Data

Jan. 22, 2018 (DE) .......................... 102018101313.2

(51) Int. Cl.
*A61B 5/145* (2006.01)
*A61B 17/34* (2006.01)
*A61B 5/00* (2006.01)

(52) U.S. Cl.
CPC ........ *A61B 5/14503* (2013.01); *A61B 5/0053* (2013.01); *A61B 5/14514* (2013.01); *A61B 5/14532* (2013.01); *A61B 5/14542* (2013.01); *A61B 5/6849* (2013.01); *A61B 5/6879* (2013.01); *A61B 17/3468* (2013.01); (Continued)

(58) Field of Classification Search
CPC ............ A61B 5/14503; A61B 5/14514; A61B 5/14535; A61B 5/14539; A61B 5/14542; A61B 5/6849; A61B 5/6879; A61B 5/14546; A61B 5/0053; A61B 5/14507; A61B 5/683; A61B 5/14532; A61B 17/3468; A61B 2562/14; A61B 2562/146; A61B 2560/063; A61B 2560/045; A61M 2005/1585; A61M 2205/3507; A61M 2230/20; A61M 2230/201
See application file for complete search history.

(56) References Cited

U.S. PATENT DOCUMENTS

2004/0133164 A1 7/2004 Funderburk et al.
2013/0267811 A1 10/2013 Pryor et al.
(Continued)

FOREIGN PATENT DOCUMENTS

DE 102018101275 7/2019
WO 2006092317 9/2006
WO 2016128334 8/2016

*Primary Examiner* — Patrick Fernandes
(74) *Attorney, Agent, or Firm* — Volpe Koenig

(57) ABSTRACT

A system for analyzing a patient using a transcutaneous sensor, having a base unit for attaching to the patient, an injector, releasably connectable to the base unit, for the transcutaneous insertion of the sensor into the patient, and a detection unit, releasably connectable to the base unit, for generating measurement data by the sensor. The base unit has a holding device which is configured to cooperate with the injector and detection unit such that, in a detection configuration with the detection unit arranged on the base unit, a contact pressure is applied to the sensor by the holding device for frictional fixing, and in an injection configuration with the injector arranged on the base unit, a lower contact pressure than in the detection configuration is applied to the sensor by the holding device.

14 Claims, 5 Drawing Sheets

(52) U.S. Cl.
CPC ....... *A61B 5/14507* (2013.01); *A61B 5/14546* (2013.01); *A61B 5/683* (2013.01); *A61B 2560/045* (2013.01); *A61B 2560/063* (2013.01); *A61B 2562/14* (2013.01); *A61M 2205/3507* (2013.01); *A61M 2230/201* (2013.01)

(56) References Cited

U.S. PATENT DOCUMENTS

| | | | |
|---|---|---|---|
| 2013/0267813 A1* | 10/2013 | Pryor | A61B 5/6849 |
| | | | 600/365 |
| 2014/0187876 A1* | 7/2014 | Ohkoshi | A61B 5/14532 |
| | | | 600/309 |
| 2017/0112532 A1 | 3/2017 | Schoonmaker et al. | |
| 2017/0188912 A1* | 7/2017 | Halac | A61B 5/6849 |
| 2017/0265791 A1 | 9/2017 | Pace et al. | |
| 2017/0303831 A1* | 10/2017 | Tsubouchi | A61B 5/14546 |
| 2018/0014762 A1 | 1/2018 | Brister et al. | |

\* cited by examiner

SYSTEM FOR ANALYZING A PATIENT USING A TRANSCUTANEOUS SENSOR

INCORPORATION BY REFERENCE

The following documents are incorporated herein by reference as if fully set forth: German Patent Application No. 10 2018 101 313.2, filed Jan. 22, 2018.

BACKGROUND

The invention relates to a system for analyzing a patient using a transcutaneous sensor.

For many medical applications it is necessary to insert a sensor into a patient, in particular in order to obtain readings from the patient, for example glucose levels or lactose levels.

U.S. 2004/0133164 A1 discloses a system for analyzing a patient using a transcutaneous sensor, which comprises a base unit, an injector and a detection unit. The base unit is stuck to the patient's skin. Subsequently, the injector can be fitted on the base unit in order to transcutaneously inject a sensor. Subsequently, the injector is removed from the base unit and the detection unit arranged on the base unit, such that, by the sensor, glucose levels of the patient can be determined by the detection unit.

After being transcutaneously injected, the sensor is bent and clamped in place between a baseplate and a cover in order to be fixed.

However, more freedom in terms of the geometry and material characteristics of the sensor is desirable. Furthermore, the patient may experience discomfort when the sensor is bent.

The present invention is based on the object of providing a system for analyzing a patient using a transcutaneous sensor, said system allowing the sensor to be held securely with the detection unit arranged while having low requirements in terms of geometry and material characteristics of the sensor. Furthermore, discomfort upon arranging the detection unit is intended to be avoided.

SUMMARY

This object is achieved by a system for analyzing a patient with a transcutaneous sensor with one or more features of the invention. Advantageous configurations of the system according to the invention are described below and in the claims.

The system according to the invention for analyzing a patient using a transcutaneous sensor has a base unit for attaching to the patient, an injector, releasably connectable to the base unit, for the transcutaneous insertion of the sensor into the patient, and a detection unit, releasably connectable to the base unit, for generating measurement data via the sensor.

The system according to the invention can thus be basically handled as known, in that the base unit is arranged on the patient, in particular stuck to the patient's skin. In the process, the injector can already be arranged on the base unit while the base unit is being attached to the patient. Equally, the base unit can first of all be attached to the patient and subsequently the injector is arranged on the base unit. By use of the injector, the sensor is injected into the patient, particularly preferably transcutaneously injected. Subsequently, the injector is removed from the base unit and the detection unit is arranged on the base unit in order to obtain measurement data, in particular in order to determine glucose or lactose levels of the patient.

What is essential is that the base unit has a holding device which is configured to cooperate with the injector and detection unit such that, in a detection configuration with the detection unit arranged on the base unit, a contact pressure is applied to the sensor by the holding device for frictional fixing, and in an injection position with the injector arranged on the base unit, a lower contact pressure than in the detection configuration is applied to the sensor by the holding device.

The base unit thus has a holding device. The latter, as a constituent part of the base unit, is arranged together with the former on the patient and is thus located on the patient even in the injection configuration. In the injection configuration, however, a lower contact pressure than in the detection configuration, particularly preferably no contact pressure, is applied to the sensor by the holding device.

Therefore, as a result of the contact pressure being applied to the sensor in the detection configuration, the present invention thus allows the sensor to be fixed, thereby allowing secure transmission of measurement data between the sensor and detection unit and furthermore saving the patient discomfort, since, as a result of the fixing, the sensor does not move or at least moves to a reduced extent relative to the base unit and even during use it is not necessary for the user to arrange a separate holding element and/or to work on, in particular bend, the sensor.

The holding device has preferably at least one lever element which is arranged and configured such that the lever element is movable in the direction of the sensor by the detection unit being attached. As a result, higher contact pressure on the sensor is obtained in the detection configuration than in the injection configuration in a structurally uncomplicated manner.

Preferably, the holding device has an elastic restoring element which cooperates with the lever element and is configured to generate a restoring force, away from the sensor, on the lever element. As a result, a basic position of the lever element, in which the lever element does not exert or exerts only a low contact pressure on the sensor, is formed in a structurally simple manner. The detection unit and lever element are configured so as to cooperate in such a way that, when the detection unit is arranged on the base unit, the lever element is moved in the direction of the sensor, such that the restoring force of the elastic restoring element is overcome and a contact pressure on the sensor is generated.

It is within the scope of the invention that the holding device has at least one stop element which is arranged such that, when the lever element is moved in the direction of the sensor, the sensor is located between the lever element and stop element, such that a contact pressure is applied to the sensor between the stop element and lever element. In particular, it is advantageous for the stop element to be arranged, starting from the lever element, on the opposite side of the sensor from the lever element.

In an advantageous development, the holding device has several lever elements. As a result, a higher and/or more uniform contact pressure on the sensor can be achieved. Preferably, each of the lever elements has an elastic restoring element. In this case, a common elastic restoring element can apply a restoring force, away from the sensor, for each lever element. Preferably, each lever element is assigned a separate elastic restoring element.

The plurality of lever elements are arranged preferably in a manner surrounding the sensor. As a result, a contact pressure can be applied between the lever elements in a structurally simple manner, without stop elements being necessary.

Preferably, the injector is configured to insert the sensor into the patient, in particular transcutaneously, in an injection direction along an injection axis. The injection axis is preferably perpendicular to a main plane of the base unit, which main plane is parallel to the patient's skin at the site of the injection.

Preferably, the lever elements are arranged in a common plane, particularly preferably in a common plane perpendicular to the injection axis.

The lever elements are arranged preferably in a circle which encloses the sensor. In particular, the sensor is located preferably at the center of this circle. Preferably, the lever elements are arranged in a uniformly distributed manner on the circumference of the circle, i.e. in each case two adjacent lever elements enclose preferably an identical angle with the center of the circle.

Therefore, the lever elements are arranged in a manner surrounding the sensor preferably in a ring, particularly preferably in a uniformly distributed manner. The detection unit has preferably a pressing surface which is arranged such that, when the detection unit is arranged on the base unit, a contact pressure is applied to the holding element, in particular in the direction of the sensor.

As a result, in a structurally simple manner, when the detection unit is arranged on the base unit, a contact pressure is applied to the holding device by the pressing surface and thus the holding device is moved in the direction of the sensor.

In an advantageous embodiment, the holding device exhibits an elastic material. The elastic material is configured to be passed through by the sensor. The elastic material can be formed without an opening for the sensor in the delivery state and in this case is passed through by the injector during the injection operation.

However, it is advantageous for the elastic material to have a passage opening for the sensor, said opening being configured to bear against the sensor in a frictionally engaged manner, in particular for an interference fit.

The elastic material allows additional fixing of the sensor. Furthermore, a contact pressure can be obtained in a structurally simple manner by exertion of pressure on the elastic material.

In particular, it is advantageous for at least one, in particular several lever elements to be arranged on or in the elastic material.

For stable, releasable arrangement on the base unit, the base unit and detection unit and/or base unit and injector are configured to be releasably connected by a bayonet coupling.

The holding device is preferably configured to cooperate with the injector such that, in an injection position, the sensor is arrangeable so as to pass through the holding device. As a result, an arrangement which allows the exertion of a contact pressure on the sensor when the detection unit is arranged on the base unit is produced in a structurally uncomplicated manner.

The injector is preferably configured so as to cooperate with the base unit such that, after completion of the injection operation, the sensor has been transcutaneously injected and is thus located partially in the tissue of the patient and partially outside the latter. When the detection unit is subsequently arranged on the base unit, the part located outside the tissue of the patient is fixed by the holding device of the base unit by way of the increased contact pressure.

Preferably, in the detection configuration with the sensor in the injection position (after completion of the injection operation), the detection unit is configured to bear against the sensor with a coupling element of the detection unit.

It is within the scope of the invention that the sensor is an electric sensor and has electrical terminals. Accordingly, the coupling element of the detection unit can have electrical contacts, which are configured such that, when the detection unit is arranged on the base unit, the electrical contacts are conductively connected to corresponding electrical contacts of the sensor.

The system according to the invention is suitable in particular for the use of an optical sensor. Such sensors have typically at a proximal end a region of which the optical property changes depending on the substances to be detected in the tissue of the patient. This proximal region is located in the tissue of the patient in the injection position of the sensor. In a distal region, which is located outside the tissue of the patient in the injection position of the sensor, information can be transmitted optically. In particular, it is advantageous for the sensor to be configured to couple radiation, in particular light, in and out in a distal region, in particular at the distal end. The coupling element is, in this preferred embodiment, configured to couple radiation in and out at the distal end of the sensor, in particular to couple light in and out. The coupling element is thus preferably in the form of an optical coupling element. The basic principles of such optical measurement are described in WO2016128334A1 and WO2006092317A1.

The insertion, in particular transcutaneous insertion, of the sensor takes place preferably by a hollow needle. In this case, the use of a closed hollow needle with a lumen or a slotted hollow needle which has a slot at least in the proximal region of the hollow needle, which passes into the patient, is within the scope of the invention.

The injector is preferably configured such that, during the injection operation, the hollow needle with the sensor passes transcutaneously into the tissue of the patent and subsequently only the hollow needle, but not the sensor, is withdrawn from the tissue of the patient again. Preferably, in this case, the sensor is held by a holding element of the injector, in order to prevent the sensor from being withdrawn, in particular as described in DE102018101275.6 or DE102018101283.7.

Therefore, in the injection configuration, the holding device is preferably configured to be passed through by a hollow needle of the injector. In particular, in the advantageous embodiment when an elastic material is provided, the elastic material is configured to be passed through by the hollow needle.

BRIEF DESCRIPTION OF THE DRAWINGS

Further preferred features and embodiments are explained in the following text on the basis of an exemplary embodiment and figures, in which.

DETAILED DESCRIPTION

In the figures, identical reference signs denote identical or functionally identical elements.

Figure 3:
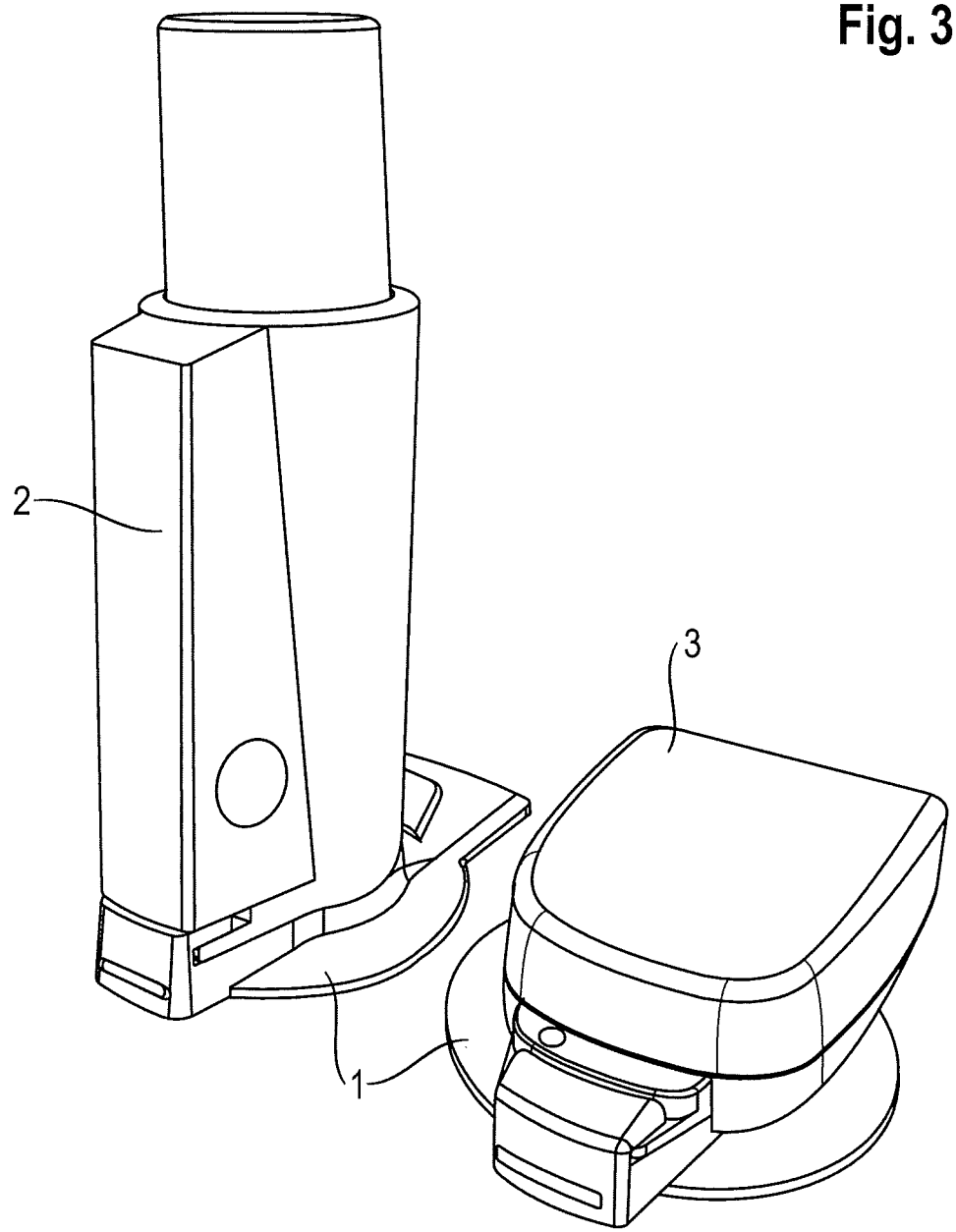
FIG. 3 shows an injector and a detection unit of the exemplary embodiment, which are each arranged on a base unit, in a perspective illustration.

The figures illustrate an exemplary embodiment of a system according to the invention for analyzing a patient using a transcutaneous sensor. As can be seen in particular in FIG. 3, the system comprises a base unit 1 for attaching to the patient, an injector 2, releasably connectable to the base unit, for the transcutaneous insertion of a sensor 5 into the patient, and a detection unit 3, releasably connectable to the base unit 1, as a detection element for generating measurement data by the sensor 5. In FIG. 3, for reasons of greater clarity, the base unit 1 has been illustrated twice, once with the injector 2 arranged and once with the detection unit 3 arranged.

Figure 2:
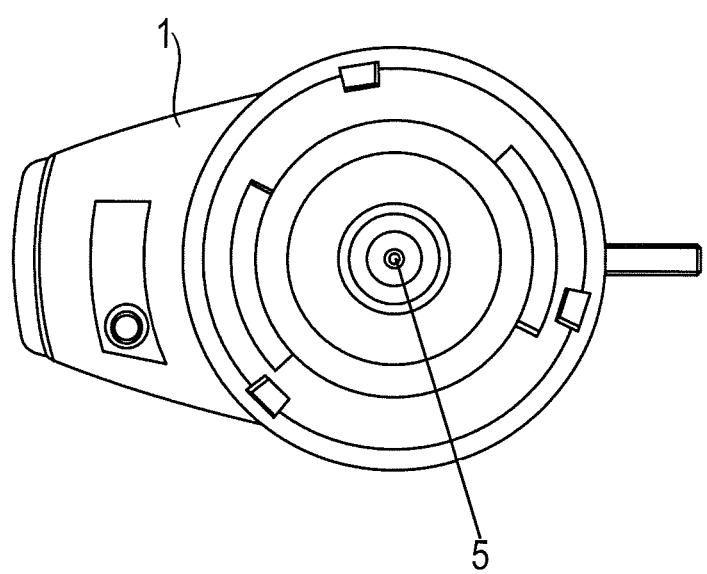
FIG. 2 shows the base unit in a plan view from below.

During use, the base unit 1 is stuck to the patient's skin with the underside illustrated in plan view in FIG. 2. In the present exemplary embodiment, this takes place with the injector 2 already arranged on the base unit 1. It is equally possible for the base unit to be arranged on the patient first and subsequently for the injector to be connected to the base unit.

The base unit 1 has a holding device 4 which is configured to cooperate with the injector 2 and detection unit 3, such that, in a detection configuration with the detection unit arranged on the base unit, a contact pressure is applied to the sensor 5 by the holding device for frictional fixing, and in an injection configuration with the injector arranged on the base unit, a lower contact pressure than in the detection configuration is applied to the sensor 5 by the holding device 4. This is explained in more detail in the following text with reference to the figures.

Figure 1:
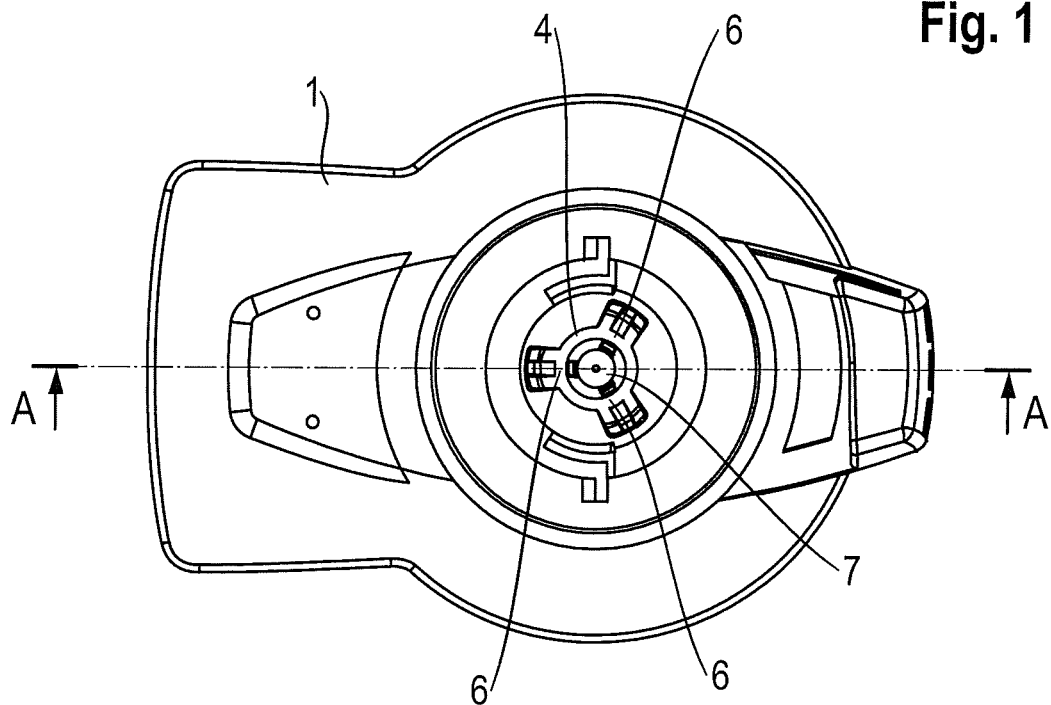
FIG. 1 shows a base unit of the exemplary embodiment in a plan view from above.

As is apparent from FIG. 1, the holding device 4 is arranged in the center of several concentrically arranged annular elements. The outer annular elements serve to form a bayonet coupling when the injector 2 or the detection unit 3 is arranged on the base unit 1. Located centrally in this concentric arrangement is the holding device 4. The latter has, in the present exemplary embodiment, three lever elements 6, which are partially embedded in an elastic compound 7.

As is apparent from FIG. 1 in the plan view from above, the elastic compound 7 surrounds a central cylindrical cutout which, in the plan view from above according to FIG. 1, is perpendicular to the plane of the drawing. During the injection operation, this cylindrical cutout is passed through by a hollow needle 8 of the injector together with the sensor 5 and after the injection operation, the transcutaneously injected sensor 5 passes through the elastic compound 7 at the location of the cylindrical cutouts. On a circle, the center of which corresponds to the cylindrical cutout, the three lever elements 6 are arranged in a uniformly distributed manner, that is to say that in each case two adjacent lever elements 6 each enclose the same angle, in the present case 120°, with the center of the circle (of the cylindrical cutout).

It is apparent from the plan view from below according to FIG. 2 that, in the region of the cylindrical cutout, the base unit 1 has a circular opening such that the hollow needle 8 and sensor 5 (which are illustrated for example in FIG. 5) can pass through the base unit 1 at this opening. In this exemplary embodiment, the injection thus takes place along an injection axis, which is perpendicular to the plane of the drawing in FIGS. 1 and 2, and takes place at the location of the cylindrical cutout in the elastic compound 7, or at the location of the sensor 5 illustrated in FIG. 2.

Figure 4:
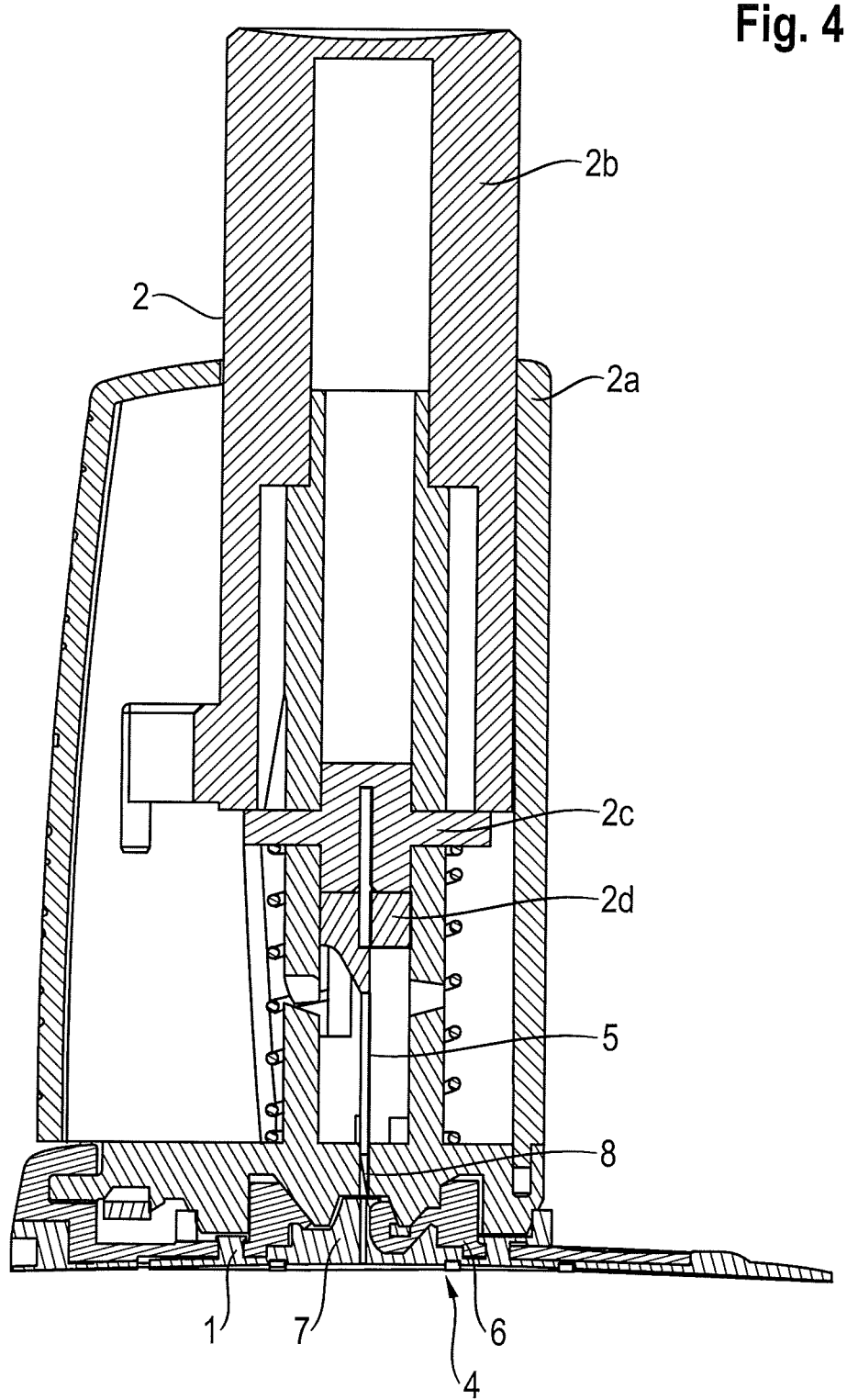
FIG. 4 shows a sectional illustration of the injector arranged on the base unit before injection on the section line A-A in FIG. 1.

FIG. 4 illustrates a section through the injector 2 arranged on the base unit 1. The section plane is perpendicular to the illustrations according to FIG. 1 and FIG. 2 and has been chosen such that the injection axis and the sensor lie in the section plane. In FIG. 1, the section plane is indicated by A-A.

The injector 2 has a base element 2a and elements that are arranged in a displaceable manner on the base element, namely a sliding element 2b, hollow-needle top part 2c and holding element 2d. During the injection operation, the sliding element 2b is depressed by the user. This movement is transmitted to the hollow needle 8 via the hollow-needle top part 2c, the hollow needle 8 being arranged on the hollow-needle top part 2c. The hollow needle 8 is in the form of a slotted hollow needle and has, in a proximal region, a continuous slot. Arranged beneath the hollow-needle top part 2c is the holding element 2d. The latter has a cam, which engages through the slot into the hollow needle. The sensor 5 is arranged in the hollow needle in the slotted region beneath the cam of the holding element 2d. The sliding movement triggered by the user is transmitted also to the holding element 2d via the sliding element 2b and the hollow-needle top part 2c, such that a relative movement between the sensor 5 and hollow needle 8 is avoided during the injection operation, since the sensor 5 is upwardly in abutment with the cam of the holding element 2d.

Thus, by way of the above-mentioned sliding movement, in particular the hollow needle 8 and sensor 5 are displaced along the injection axis and pass through the elastic compound 7 in the region of the cylindrical opening and thus also through the holding device 4.

Figure 5:
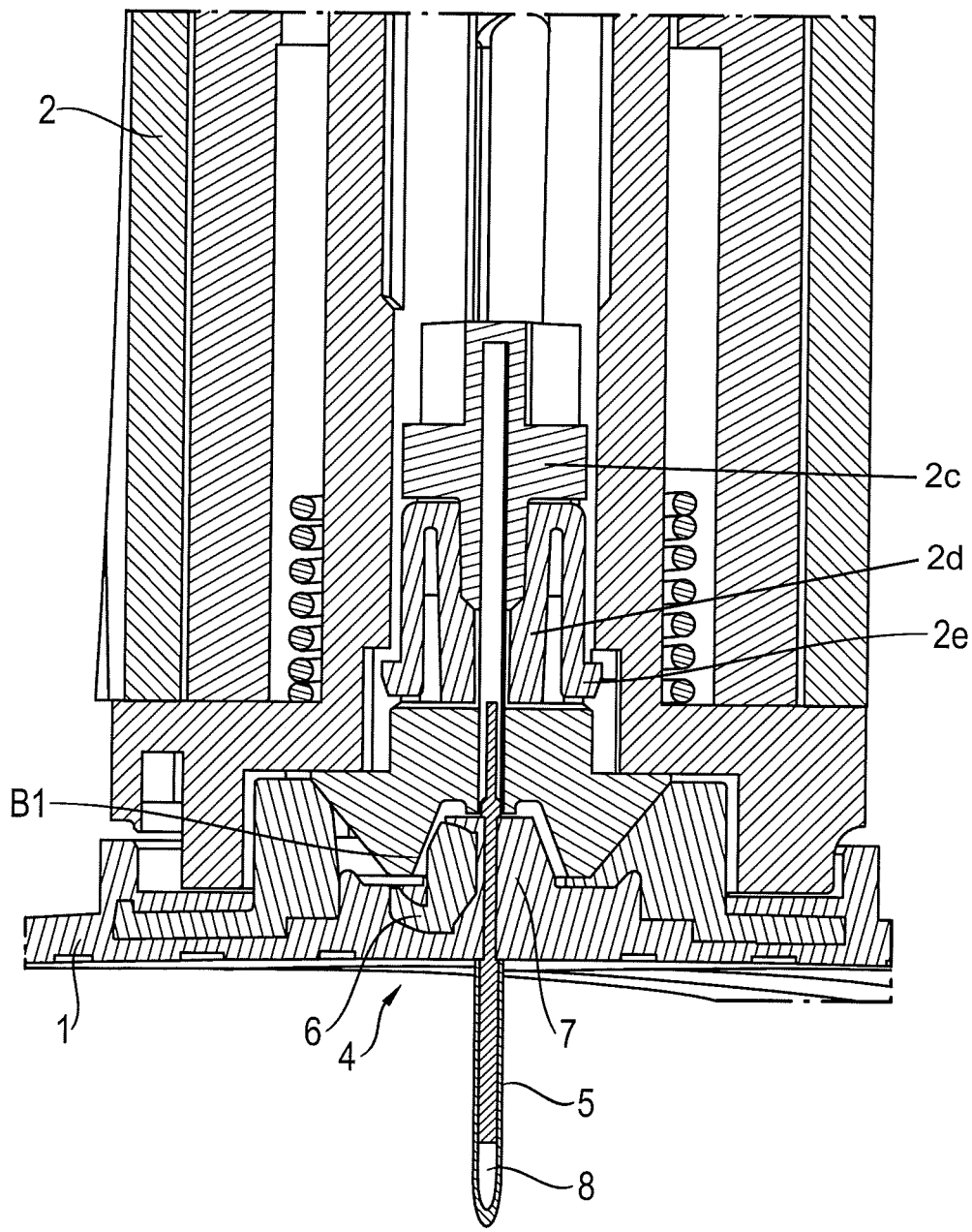
FIG. 5 shows a detail of FIG. 4 following insertion of a hollow needle of the injector into a tissue of the patient along a section line approximately perpendicular to A-A in FIG. 1.

As is apparent from FIG. 5, the injector 2 has, in its lower region B1, a conical face, which is thus apparent as an inclined face in the sectional illustration according to FIG. 5. What is essential is that, in this region B1, there is no contact or at least no force transmission between the inclined face and the lever element 6. Thus, with the injector 2 arranged on the base element 1, no contact pressure is applied to the lever elements 6.

FIG. 5 illustrates the state after transcutaneous insertion of the hollow needle 8 and sensor 5. Subsequently, a countermovement takes place manually by the sliding element being withdrawn by the user or by a preloaded injection spring being released, at least the hollow-needle top part 2c being displaced upward along the injection axis during said countermovement. In the depressed state, the holding element 2d latches with the base element 2a of the injector 2 by way of latching elements 2e, however, such that the holding element 2d is not displaced upward. This ensures that when the hollow needle 8 is withdrawn, the senor 5 is not withdrawn, since the cam of the holding element 2d, said cam being arranged above the sensor 5 and engaging in the slot of the hollow needle 8, prevents the sensor from being withdrawn upward.

The injector is configured preferably as described in DE102018101275.6 or DE10 2018 101 283.7.

Following completion of the injection operation, the hollow needle 8 is thus located within the injector 2 again, but the sensor 5 passes through the holding device 4 and in particular the elastic compound 7 and has been injected transcutaneously into the tissue of the patient. In this state, no contact pressure is applied to the sensor 5 by the lever elements 6. The cylindrical opening in the elastic compound 7 has a slightly smaller diameter than the sensor 5, and so there is a slight interference fit of the sensor 5 in the elastic compound 7.

Subsequently, the injector 2 is released from the base unit 1 and the detection unit 3 is arranged on the base unit 1 likewise by a bayonet coupling. As is apparent from FIG. 6, the detection unit 3 likewise has a conically formed region, which is apparent as an inclined face in the sectional illustration according to FIG. 6, in particular in the region B2. In contrast to the conical region of the injector 2, the conical region of the detection unit 3 is formed in a tighter manner, however, such that when the detection unit 3 is arranged on the base unit 1, a contact pressure is applied to the lever elements 6. It is apparent from FIG. 6 that the lever element 6 has been displaced in the direction of the sensor 5, due to the abutment against the inclined face of the detection unit 3 in the region B2. Although the lever element 6 does not bear directly on the sensor 5 in this exemplary embodiment, a considerable contact pressure is transmitted to the sensor 5 via the elastic compound 7. The small region of elastic compound 7 between the sensor 5 and lever element 6 additionally allows pressure equalization and prevents the sensor 5 from being damaged by the contact pressure on account of the hard consistency of the lever element 6. It is equally possible, in an alternative exemplary embodiment, for the lever elements to bear directly on the sensor 5.

Figure 6:
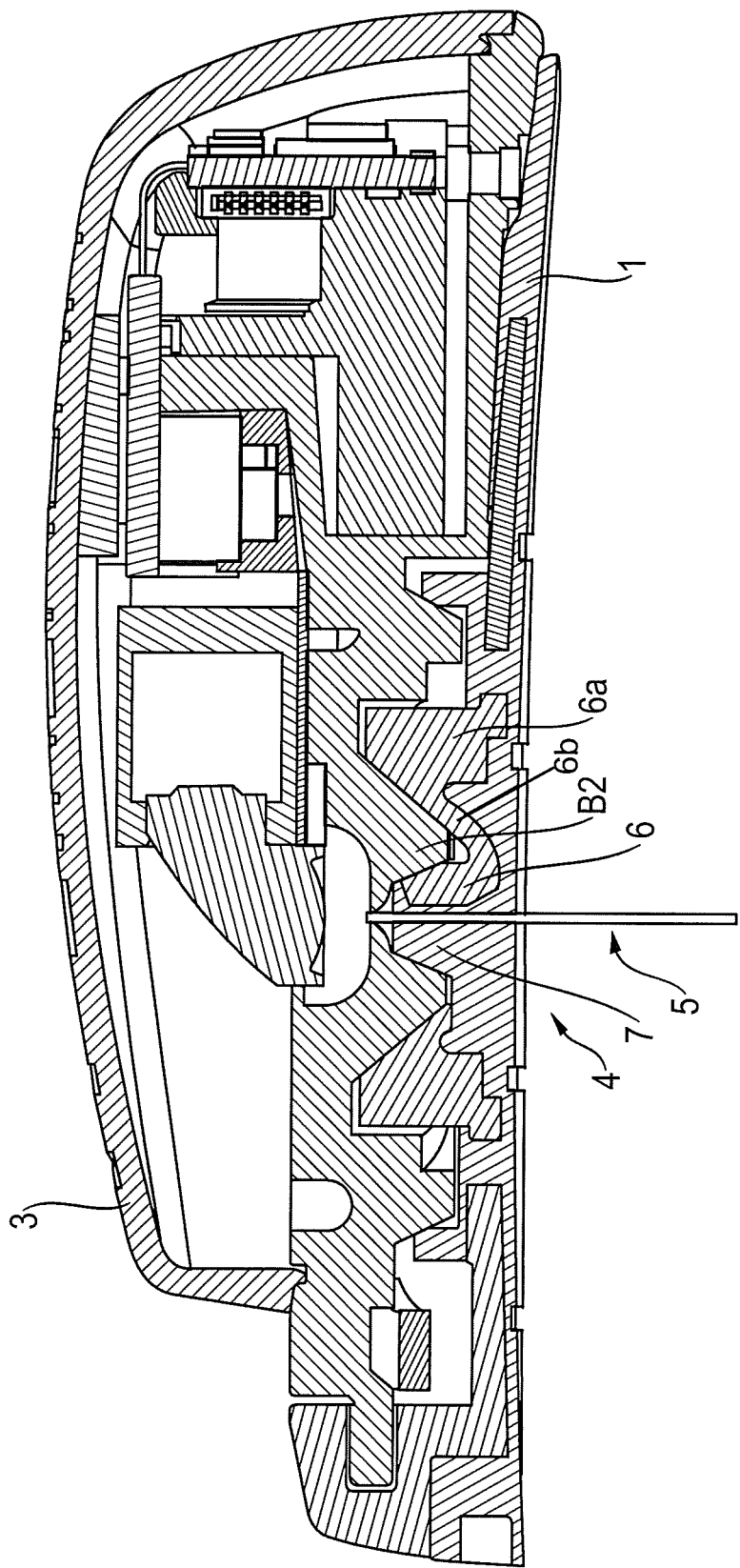
FIG. 6 shows a sectional illustration of the detection unit arranged on the base unit on the section line A-A in FIG. 1.

As is apparent in particular from FIG. 6, the lever element 6 has a fastening region 6*a*. The latter is connected in a fixed location to the base unit 1. Formed between the fastening region 6*a* and that region of the lever element 6 that faces the sensor 5 is an elastic region, which thus acts as an elastic restoring element 6*b*. This restoring element 6*b* is configured such that, without external pressure, the lever element 6 is in the basic position according to FIGS. 4 and 5 and thus does not exert any contact pressure on the sensor 5. When the detection unit 3 is arranged, by contrast, the restoring force of the elastic restoring element 6*b* is overcome, in order for the contact pressure to applied to the sensor 5 by the three lever elements 6.

The invention claimed is:

1. A system for analyzing a patient using a transcutaneous sensor, the system comprising:
    a base unit (1) adapted to be attached to the patient,
    an injector (2), releasably connectable to the base unit (1), adapted for transcutaneous insertion of the sensor into the patient,
    a detection unit housing, releasably connectable to the base unit (1),
    the base unit (1) has a holding device (4) which is configured to cooperate with the injector (2) and the detection unit housing such that, in a detection configuration with the detection unit housing arranged on the base unit (1), a contact pressure is applied to the sensor (5) by the holding device (4) for frictional fixing, and in an injection configuration with the injector (2) arranged on the base unit (1), a lower contact pressure than in the detection configuration is applied to the sensor (5) by the holding device (4), wherein the holding device (4) includes at least one lever element (6) arranged and configured to be movable in a direction of the sensor by the detection unit housing (3) being attached to the base unit (1), the sensor (5) is supported by an elastic compound that surrounds a portion of the sensor (5), and the at least one lever element (6) is configured to be displaced against the elastic compound by a portion of the detection unit housing for the frictional fixing of the sensor (5) such that the at least one lever element (6) does not bear directly on the sensor (5).

2. The system according to claim 1, wherein the elastic compound (7) is configured to generate a restoring force, away from the sensor (5), on the at least one lever element (6).

3. The system according to claim 2, wherein the at least one lever element (6) of the holding device (4) comprises several lever elements which are arranged surrounding the sensor (5).

4. The system according to claim 3, wherein the lever elements are arranged in a ring surrounding the sensor (5).

5. The system according to claim 4, wherein the lever elements are uniformly distributed around the ring.

6. The system according to claim 1, wherein the detection unit housing includes a pressing surface which is arranged such that, when the detection unit housing is arranged on the base unit (1), a contact pressure is applied to the holding device (4).

7. The system according to claim 6, wherein the contact pressure is applied in a direction of the sensor.

8. The system according to claim 1, wherein the holding device (4) includes an elastic material which is configured to be passed through by the sensor (5).

9. The system according to claim 8, wherein the elastic material has a passage opening for the sensor (5), said opening being configured such that the elastic material around the opening bears against the sensor (5) in a frictionally engaged manner.

10. The system according to claim 1, wherein at least one of the base unit (1) and detection unit housing or the base unit (1) and the injector (2) are configured to be releasably connected by a bayonet coupling.

11. The system according to claim 1, wherein, in an injection position, the sensor (5) is arranged to pass through the holding device (4).

12. The system according to claim 1, wherein, in the detection configuration with the sensor (5) in an injection position, the detection unit housing bears against the sensor (5) with a coupling element of the detection unit (3).

13. The system according to claim 12, wherein the coupling element comprises an optical coupling element.

14. The system according to claim 1, wherein, in the injection configuration, the holding device (4) is adapted to be passed through by a hollow needle (8) of the injector.

* * * * *